(12) United States Patent
Hibino et al.

(10) Patent No.: US 7,511,171 B2
(45) Date of Patent: Mar. 31, 2009

(54) METHOD FOR PRODUCING CARBOXYLIC ACID COMPOUND

(75) Inventors: Hiroaki Hibino, Toyonaka (JP); Tomoyasu Yoshida, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 97 days.

(21) Appl. No.: 10/594,501

(22) PCT Filed: Mar. 29, 2005

(86) PCT No.: PCT/JP2005/006578

§ 371 (c)(1),
(2), (4) Date: Sep. 28, 2006

(87) PCT Pub. No.: WO2005/095319

PCT Pub. Date: Oct. 13, 2005

(65) Prior Publication Data

US 2007/0197824 A1   Aug. 23, 2007

(30) Foreign Application Priority Data

Apr. 1, 2004   (JP) .............................. 2004-108760

(51) Int. Cl.
*C07C 65/01* (2006.01)
(52) U.S. Cl. ...................................... 562/475
(58) Field of Classification Search ................. 560/1
See application file for complete search history.

(56) References Cited

U.S. PATENT DOCUMENTS

| | | | | |
|---|---|---|---|---|
| 5,587,483 A * | 12/1996 | Johnson et al. | ............. | 548/252 |
| 5,675,036 A | 10/1997 | Fukuda et al. | | |
| 6,861,566 B2 | 3/2005 | Hibino et al. | | |

FOREIGN PATENT DOCUMENTS

| JP | 03095144 A2 | 4/1991 |
|---|---|---|
| JP | 09077717 A2 | 3/1997 |
| JP | 10330313 A2 | 12/1998 |

* cited by examiner

*Primary Examiner*—Paul A Zucker
(74) *Attorney, Agent, or Firm*—Foley & Lardner LLP

(57) ABSTRACT

The present invention provides a method for producing a compound represented by the formula (3):

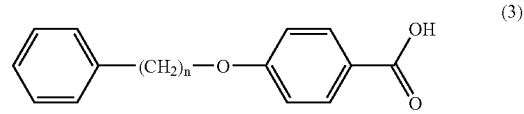

wherein n is an integer of 1 to 6, characterized by the steps of hydrolyzing a solution containing an ester compound represented by the formula (1):

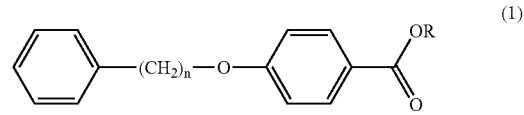

wherein R is a lower alkyl group and n is an integer of 1 to 6, and a compound represented by the formula (2):

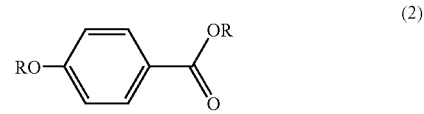

wherein R is as defined above, adjusting the pH of the resulting solution to pH 4 to 8, and then subjecting to phase separation to obtain an organic layer containing the carboxylic acid of formula (3).

8 Claims, No Drawings

METHOD FOR PRODUCING CARBOXYLIC ACID COMPOUND

FIELD OF THE INVENTION

The present invention relates to a method for producing a carboxylic acid compound.

RELATED BACKGROUND ART

Carboxylic acid compounds including 4-(4-phenylbutoxy) benzoic acid of formula (3):

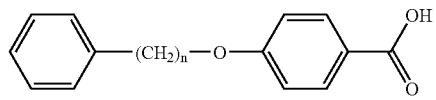

(3)

wherein n is an integer of 1 to 6, are useful as intermediates of medicines (see, for example, Patent Document 1). As a production method thereof, for example, a method in which an ester compound represented by the formula (4):

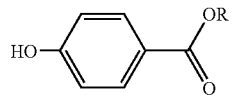

(4)

wherein R is a lower alkyl group, and a halogen compound represented by the formula (5):

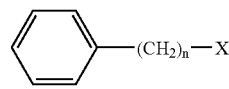

(5)

wherein n is an integer of 1 to 6 and X is a halogen atom, are reacted in an organic solvent in the presence of a base, and then the reaction mixture is hydrolyzed is known (see, for example, Patent Document 1). According to this method, however, not only the reaction of the ester compound represented by the formula (4) and the halogen compound represented by the formula (5), but also a side reaction shown in the following scheme 1:

Scheme 1

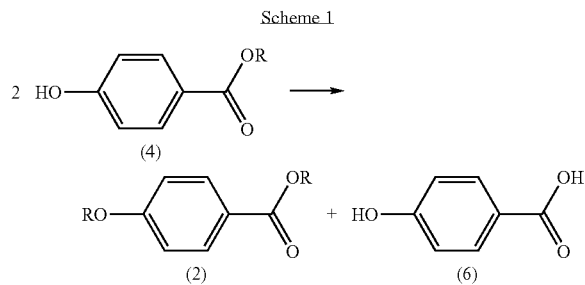

progresses, and thus, in addition to a desired ester compound represented by the formula (1)

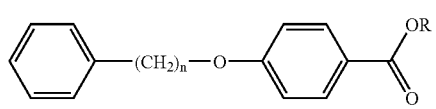

(1)

wherein R and n are as defined above, a compound represented by the formula (2):

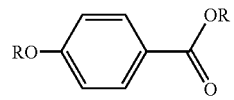

(2)

wherein R is as defined above, and a compound represented by the formula (6):

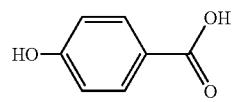

(6)

are also produced. Among these by-products, since the compound represented by the formula (2) has a similar chemical structure to that of the ester compound represented by the formula (1), it is difficult to separate the compound from the ester compound represented by the formula (1). In addition, when a mixture containing the ester compound represented by the formula (1) and the compound represented by the formula (2) is hydrolyzed, the compound represented by the formula (2), in addition to the ester compound represented by the formula (1), is hydrolyzed to a carboxylic acid represented by the formula (7):

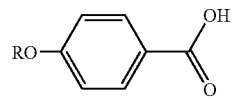

(7)

wherein R is as defined above, which leads to a problem in that the carboxylic acid is contaminated in the objective carboxylic acid compound represented by the formula (3).

Patent Document 1: Japanese Patent Application Laid-open Publication No. 3-95144

DISCLOSURE OF THE INVENTION

Under such a circumstance, in order to develop a method for producing the carboxylic acid compound represented by the formula (3) from a mixture containing the ester compound represented by the formula (1) and the compound represented by the formula (2) as a starting material wherein the obtained reaction mixture contains a reduced amount of the carboxylic acid represented by the formula (7), the present inventors have studied. As a result, they have found that when after the above-mentioned mixture is hydrolyzed, the resulting mixture is adjusted to pH 4 to 8 and liquid phase separation is conducted, the by-product carboxylic acid represented by the formula (7) is easily removed into an aqueous layer, and the amount of the carboxylic acid represented by the formula (7) contaminated in the organic layer containing the carboxylic acid compound represented by the formula (3) can be reduced; and have accomplished the present invention.

That is, the present invention provides a method for producing a compound represented by the formula (3):

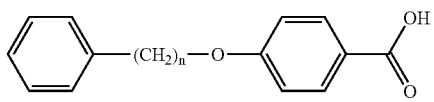

wherein n is an integer of 1 to 6, characterized by the steps of hydrolyzing a solution containing an ester compound represented by the formula (1):

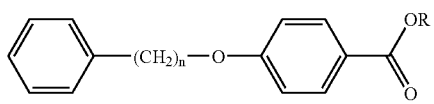

wherein R is a lower alkyl group and n is an integer of 1 to 6, and a compound represented by the formula (2):

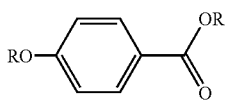

wherein R is as defined above, adjusting the pH of the resulting solution to pH 4 to 8, and then subjecting to phase separation to obtain an organic layer containing the carboxylic acid of formula (3).

BEST MODE FOR CARRYING OUT THE INVENTION

In the ester of formula (1):

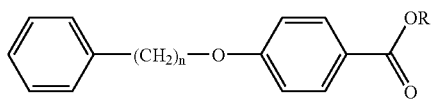

hereinafter referred to as the "ester compound (1)", R is a lower alkyl group, and n is an integer of 1 to 6. Examples of the lower alkyl group include, for example, linear or branched alkyl groups having 1 to 3 carbon atoms, such as methyl group, ethyl group, n-propyl group, or isopropyl group.

Examples of the ester compound (1) include, for example, methyl 4-benzyloxybenzoate,
methyl 4-(2-phenylethoxy)benzoate,
methyl 4-(3-phenylpropoxy)benzoate,
methyl 4-(4-phenylbutoxy)benzoate,
methyl 4-(5-phenylpentyloxy)benzoate,
methyl 4-(6-phenylhexyloxy)benzoate,
ethyl 4-(4-phenylbutoxy)benzoate,
n-propyl 4-(4-phenylbutoxy)benzoate,
isopropyl 4-(4-phenylbutoxy)benzoate, and the like.

Examples of the compound represented by the formula (2):

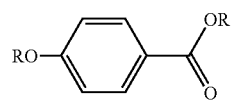

wherein R is as defined above (hereinafter referred to as the "compound (2)") include, for example, methyl 4-methoxybenzoate, ethyl 4-ethoxybenzoate, n-propyl 4-n-propoxybenzoate, isopropyl 4-isopropoxybenzoate, and the like.

A mixture containing the ester compound (1) and the compound (2) is usually hydrolyzed by mixing the mixture with water, and an acid or alkali, preferably by mixing the mixture with water and an alkali. Examples of the acid include, for example, mineral acids such as hydrochloric acid, sulfuric acid or the like; and examples of the alkali include, for example, alkali metal hydroxides such as sodium hydroxide, potassium hydroxide or the like, alkaline earth metal hydroxides such as calcium hydroxide, barium hydroxide or the like. Among them, the alkali metal hydroxides are preferred.

An amount of the acid or alkali that may be used is usually 1 mole or more per mole of the ester compound (1) in the mixture. Though an upper limit thereof is not particularly restricted, using too much amount is not economical, and practically it is 5 moles or less per mole of the ester compound (1). When the mixture contains compounds reactive with the acid or alkali, the amount of the acid or alkali used is decided taking into account the amount of the compounds reactive with the acid or alkali.

An amount of water used is usually 0.2 to 10 parts by weight, preferably 0.5 to 5 parts by weight, per part of the ester compound (1). Water may be mixed with the acid or alkali beforehand.

The order of mixing the mixture containing the ester compound (1) and the compound (2), water, and the acid or alkali is not particularly limited; for example, after the mixture is mixed with water, the acid or alkali may be added thereto, or after water is mixed with the acid or alkali, the mixture may be added thereto.

A hydrolysis temperature is usually −30 to 200° C., preferably −20 to 150° C.

The hydrolysis may be carried out in an organic solvent. Examples of the organic solvent include, for example, aromatic hydrocarbon solvents such as toluene, xylene, mesitylene, chlorobenzene, dichlorobenzene or the like; ketone solvents such as methyl ethyl ketone, methyl isobutyl ketone or the like; ether solvents such as diethyl ether, methyl tert-butyl ketone or the like; alcohol solvents such as methanol, ethanol, n-propanol, isopropanol, and n-butanol; amide solvents such as N,N-dimethylformamide, N,N-dimethylacetamide, or the like N-methyl-2-pyrolidone; sulfoxide solvents such as dimethyl sulfoxide, sulfolane or the like; and phosphoryl amide solvents such as hexamethylphosphoric triamide or the like; they may be used alone or in combination. Of these, the alcohol solvents are preferable because the hydrolysis of the ester compound (1) is easily promoted in the presence of the alcohol solvent. An amount of the organic solvent used is not particularly limited. When the mixture containing the ester compound (1) and the compound (2) contains the organic solvent, the mixture can be used as it is without any problems.

After the hydrolysis of the mixture containing the ester compound (1) and the compound (2) is completed, the hydrolyzed liquid is separated while it is adjusted to pH 4 to 8, whereby a carboxylic acid, derived from the compound (2), represented by the formula (7):

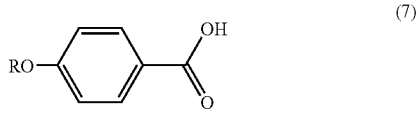

(7)

wherein R is as defined above (hereinafter referred to as the "carboxylic acid (7)") can be removed into an aqueous layer, and an organic layer containing the compound represented by the formula (3)

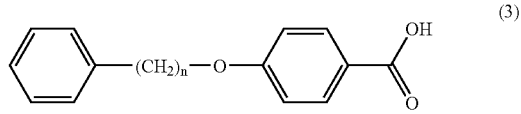

(3)

wherein n is as defined above (hereinafter referred to as the "carboxylic acid compound (3)") can be obtained. A pH of the hydrolyzed liquid is preferably adjusted to 5 to 7, from the viewpoint that the effect of removing the carboxylic acid (7) into the aqueous layer is further improved by further decreasing the amount of the carboxylic acid (7) contaminated in the organic layer. When the pH is lower than 4, the effect of removing the carboxylic acid (7) into the aqueous layer is decreased, and the amount thereof contaminated in the organic layer containing the carboxylic acid compound (3) tends to become higher. When the pH is higher than 8, the amount of the carboxylic acid compound (3) contained in the aqueous layer becomes higher, and resulted in a lower yield, and bad liquid phase separation efficiency.

The pH of the hydrolyzed liquid is adjusted by mixing the liquid with the alkali or acid according to the pH of the hydrolyzed liquid. For example, when the hydrolysis is conducted using an acid, the hydrolyzed liquid may be mixed with an alkali to adjust the pH, or when the hydrolysis is conducted using an alkali, the hydrolyzed liquid may be mixed with an acid to adjust the pH. Examples of the acid used in the pH adjustment include, for example, mineral acids such as hydrochloric acid, sulfuric acid, phosphoric acid or the like, and they are usually used as an aqueous solution. Examples of the alkali used in the pH adjustment include, for example, alkali metal hydroxides such as sodium hydroxide, potassium hydroxide or the like, and they are usually used as an aqueous solution.

A temperature in the pH adjustment of the hydrolyzed liquid is usually 20 to 90° C., preferably 40 to 80° C.

When the hydrolyzed liquid is not separated into two layers after the pH adjustment, a water-insoluble organic solvent is added thereto and the liquid phase separation is conducted. When the hydrolyzed solution is separated into two layers after the pH adjustment, the liquid phase separation is conducted using the solution as it is or after addition of a water-insoluble organic solvent thereto. A temperature of the liquid phase separation is usually 20 to 90° C., preferably 40 to 80° C. Examples of the water-insoluble organic solvent include, for example, aromatic hydrocarbon solvents such as toluene, xylene, mesitylene, chlorobenzene, dichlorobenzene or the like; ketone solvents such as methyl ethyl ketone, methyl isobuthyl ketone or the like; and ether solvents such as diethyl ether, methyl tert-butyl ether or the like. Among them the aromatic hydrocarbon solvents are preferable. An amount of the water-insoluble organic solvent used is not particularly limited so long as it is an amount enough to dissolve the carboxylic acid compound (3) produced by hydrolysis and capable of conducting the liquid separation. The water-insoluble organic solvent may be present in the mixture containing the ester compound (1) and the compound (2), or may be added to the mixture upon hydrolysis. In order to improve the liquid phase separation efficiency, the liquid phase separation may be conducted after adding an inorganic salt such as sodium chloride or sodium sulfate.

As to the organic layer obtained by the liquid phase separation, the above-mentioned pH adjustment and liquid phase separation may be repeated after addition of water thereto.

Thus, the organic layer containing the carboxylic acid compound (3) and a reduced amount of the carboxylic acid (7) can be obtained. The carboxylic acid compound (3) can be isolated from the organic layer, for example, by concentration. Examples of the carboxylic acid compound (3) include, for example, 4-benzyloxybenzoic acid, 4-(2-phenylethoxy) benzoic acid, 4-(3-phenylpropoxy)benzoic acid, 4-(4-phenylbutoxy)benzoic acid, 4-(5-phenylpentyloxy)benzoic acid, 4-(6-phenylhexyloxy)benzoic acid, and the like.

The mixture of starting materials used in the present invention is not particularly limited so long as the mixture comprises the ester compound (1) and the compound (2). Examples thereof include, for example, a reaction liquid obtained by reacting an ester compound represented by the formula (4):

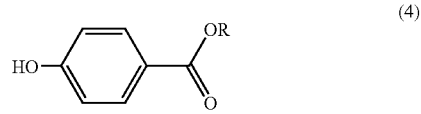

(4)

wherein R is as defined above (hereinafter referred to as the "ester compound (4)") and a halogen compound represented by the formula (5):

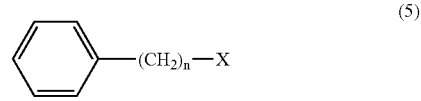

(5)

wherein n is as defined above and X is a halogen atom, hereinafter referred to as the "halogen compound (5)", in an organic solvent in the presence of a base; an organic layer obtained by mixing the above-mentioned reaction liquid, water and, if necessary, a water-insoluble organic solvent, and conducting the liquid separation; and the like.

Methods for producing the reaction liquid obtained by reacting the ester compound (4) and the halogen compound (5) in an organic solvent in the presence of a base; and the organic layer obtained by mixing the above-mentioned reaction liquid, water and, if necessary, a water-insoluble organic solvent, and conducting the liquid separation will be described below.

Examples of the ester compound (4) include, for example, methyl 4-hydroxybenzoate, ethyl 4-hydroxybenzoate, n-propyl 4-hydroxybenzoate, isopropyl 4-hydroxybenzoate, and the like.

Examples of the halogen atom include, for example, iodine atom, bromine atom, chlorine atom, and the like. Examples of the halogen compound (5) include, for example, benzyl chloride, benzyl bromide, benzyl iodide, 2-phenyl-1-chloroethane, 2-phenyl-1-bromoethane, 2-phenyl-1-iodoethane, 3-phenyl-1-chloropropane, 3-phenyl-1-bromopropane, 3-phenyl-1-iodopropane, 4-phenyl-1-chlorobutane, 4-phenyl-1-bromobutane, 4-phenyl-1-iodobutane, 5-phenyl-1-chloropentane, 5-phenyl-1-buromopentane, 6-phenyl-1-chlorohexane, 6-phenyl-1-bromohexane, and the like.

The reaction of the ester compound (4) and the halogen compound (5) proceeds well when 1 mole or more of the halogen compound (5) based on the ester compound (4), is used or when 1 mole or more of the ester compound (4) based on the halogen compound (5) is used. Accordingly, suitable amounts thereof may be decided taking into account the economic aspect and the like. The ester compound (4) is reacted in an amount of usually 1 to 5 moles, preferably 1 to 2 moles per mole of the halogen compound (5).

Examples of the organic solvent may include, for example, aromatic hydrocarbon solvents such as toluene, xylene, mesitylene, chlorobenzene, dichlorobenzene or the like; ketone solvents such as methyl ethyl ketone, methyl isobutyl ketone or the like; ether solvents such as diethyl ether, methyl tert-butyl ketone or the like; alcohol solvents such as methanol, ethanol, n-propanol, isopropanol, n-butanol or the like; amide solvents such as N,N-dimethyl formamide, N,N-dimethyl acetamide, N-methyl-2-pyrolidone or the like; sulfoxide solvents such as dimethyl sulfoxide, sulfolane or the like; and phosphoryl amide solvents such as hexamethyl phosphoric triamide or the like; they may be used alone or in combination. Among them, aprotonic polar solvents, for example, the amide solvents such as N,N-dimethyl formamide, N,N-dimethyl acetamide, N-methyl-2-pyrolidone or the like; the sulfoxide solvents such as dimethyl sulfoxide, sulfolane or the like; the phosphoryl amide solvents such as hexamethyl phosphoric triamide, or the like are preferable. An amount of the organic solvent used is usually 0.5 to 10 parts by weight, preferably 1 to 5 parts by weight, based on the ester compound (4) or the halogen compound (5) whichever used in smaller amount.

Examples of the base include, for example, alkali metal hydrides such as sodium hydride, potassium hydride or the like; alkaline earth metal hydrides such as calcium hydride or the like; alkali metal hydroxides such as lithium hydroxide, sodium hydroxide, potassium hydroxide or the like; alkaline earth metal hydroxides such as calcium hydroxide, magnesium hydroxide, barium hydroxide or the like; alkali metal carbonates such as lithium carbonate, sodium carbonate, potassium carbonate or the like; alkaline earth metal carbonates such as calcium carbonate, barium carbonate or the like; alkali metal hydrogencarbonates such as sodium hydrogencarbonate, potassium hydrogencarbonate or the like. Among them the alkali metal carbonates and the alkaline earth metal carbonates are preferable. An amount of the base used is usually 1 to 5 moles, preferably 1 to 3 moles per mole of the ester compound (4) or the halogen compound (5) whichever used in smaller amount.

A reaction temperature is usually –50 to 150° C., preferably 10 to 140° C.

The ester compound (4) and the halogen compound (5) are reacted by mixing the ester compound (4) and the halogen compound (5) in an organic solvent, and the order of mixing is not particularly limited.

After completion of the reaction, the resulting reaction liquid contains an unreacted base, salts generated by neutralizing hydrogen halides as by-products in the reaction with the base, and the like. The reaction liquid may be used as it is, or an organic layer obtained by mixing the reaction liquid, water and, if necessary, a water-insoluble organic solvent, and conducting the liquid phase separation may be used as the starting material in the above-mentioned hydrolysis.

An amount of water used in the case where the reaction liquid, water and, if necessary, a water-insoluble organic solvent are mixed, and the liquid separation is conducted, is not particularly limited. As the water-insoluble organic solvents the same solvents as cited above can be exemplified, and the amounts thereof are not particularly limited. A temperature during the liquid separation is usually 20 to 80° C.

EXAMPLES

The present invention will be described in more detail by means of Examples below, but it is not limited thereto. High performance liquid chromatography was used in the analysis.

Example 1

In a flask equipped with a stirrer were put 56.7 g of methyl 4-hydroxybenzoate, 53.8 g of potassium carbonate (anhydrous) and 108.1 g of N,N-dimethyl formamide, and the inside temperature was elevated to 110° C. After 60 g of 4-phenyl-1-chlorobutane was added dropwise at the same temperature over 2 hours, the mixture was stirred at the same temperature for 12 hours to react. 138 g of toluene was added thereto, and it was cooled until the inside temperature became not more than 80° C., to which 180 g of water was added. The inside temperature was adjusted to 65° C., and the liquid phase separation was conducted at the same temperature to give an oil layer and an aqueous layer. The oil layer was washed with 240 g of water, then 180 g of 1 wt % aqueous sodium hydroxide solution, and further 180 g of water to give 246.7 g of an oil layer containing methyl 4-(4-phenylbutoxy) benzoate. Content: 39.0% Yield: 96% (4-phenyl-1-chlorobutane basis) The oil layer contained 0.20% (area percentage) of methyl 4-methoxybenzoate.

The oil layer containing 239 g of methyl 4-(4-phenylbutoxy)benzoate, 29.3 g of methanol and 77 g of 27% by weight aqueous sodium hydroxide solution were mixed and the inside temperature was elevated to 70 to 75° C., and the mixture was stirred at the same time for 3 hours to hydrolyze it.

The hydrolyzed liquid was carefully poured into a mixture of 216.9 g of 18% by weight sulfuric acid and 175 g of toluene so that the liquid temperature was kept at not more than 70° C., and then the mixture was stirred for 15 minutes. After 45.5 g of 27% by weight aqueous sodium hydroxide solution was added thereto at an inside temperature of 65° C. to adjust the pH to 5.5, the liquid phase separation was conducted. To the obtained organic layer was added 175 g of 10 wt % aqueous sodium sulfate solution, and the liquid phase separation was conducted at an inside temperature of 65° C. and a pH of 5 to 7. The procedure of liquid phase separation using the aqueous sodium sulfate solution was further repeated twice to give an organic layer containing 4-(4-phenylbutoxy)benzoic-acid. Yield: 99.6% (methyl (4-(4-phenylbutoxy)benzoate basis)

The above-mentioned organic layer contained 4-methoxybenzoic acid as much as 0.03% (area percentage).

Example 2

In a flask equipped with a stirrer were put 35.3 g of 4-phenyl-1-chlorobutane, 33 g of methyl 4-hydroxybenzoate, 31.4 g of potassium carbonate (anhydrous), 52.5 g of N,N-dimethyl formamide and 52.5 g of toluene, then the inside temperature was elevated to 125 to 128° C., and the mixture was stirred at the same temperature for 10 hours to react. 24.5 g of toluene was added thereto, and it was cooled until the inside temperature became not more than 80° C., and water was added thereto. The inside temperature was adjusted to 65° C., and the liquid separation was conducted at the same temperature to give an oil layer and an aqueous layer. The oil layer was washed with 140 g of water, then 105 g of a 1 wt % aqueous sodium hydroxide solution, and further 105 g of water to give 138 g of an oil layer containing methyl 4-(4-phenylbutoxy)benzoate. Content: 40.5% Yield: 96% (4-phenyl-1-chlorobutane basis) The oil layer contained 0.46% (area percentage) of methyl 4-methoxybenzoate.

The oil layer containing 40 g of methyl 4-(4-phenylbutoxy)benzoate, 5.1 g of methanol and 13.6 g of 27 wt % aqueous sodium hydroxide solution were mixed and the inside temperature was elevated to 70 to 75° C., and the mixture was stirred at the same time for 3 hours to hydrolyze it.

The hydrolyzed solution was carefully poured into a mixture of 34.5 g of 10 wt % sulfuric acid and 31 g of toluene so that the liquid temperature was kept at not more than 70° C., and then the mixture was stirred for 15 minutes. After 3.9 g of 20 wt % sulfuric acid was added thereto at an inside temperature of 65° C. to adjust the pH to 6.5, the liquid separation was conducted. To the obtained organic layer was added 31 g of 10 wt % aqueous sodium sulfate solution, and the liquid phase separation was conducted at an inside temperature of 65° C. and at a pH of 6 to 7. 31 g of 10% by weight aqueous sodium sulfate solution was added thereto, and the liquid separation was conducted once more at an inside temperature of 65° C. and at a pH of 6 to 7. 31 g of water was added to the obtained organic layer and the liquid separation was conducted at an inside temperature of 65° C. and a pH of 6 to 7 to give an organic layer containing 4-(4-phenylbutoxy)benzoic acid. Yield: 98.9% (methyl 4-(4-phenylbutoxy)benzoate basis) The above-mentioned organic layer contained 4-methoxybenzoic acid in a content of not more than 0.01% (area percentage).

Comparative Example 1

In a flask equipped with a stirrer were put 33 g of methyl 4-hydroxybenzoate, 31.4 g of potassium carbonate (anhydrous) and 51.5 g of N,N-dimethyl formamide, and the inside temperature was elevated to 100° C. After 35 g of 4-phenyl-1-chlorobutane was added dropwise thereto at the same temperature over 2 hours, the mixture was stirred at the same temperature for 7 hours to react. Then, the inside temperature was elevated to 115° C., the mixture was stirred for 7 hours to react. 88 g of toluene was added thereto, and it was cooled until the inside temperature became not more than 80° C., to which 88 g of water was added. The inside temperature was adjusted to 65° C., and the liquid separation was conducted at the same temperature to give an oil layer and an aqueous layer. The oil layer was washed with 88 g of water, then a 1 wt % aqueous sodium hydroxide solution, and further water 88 g to give 147 g of an oil layer containing methyl 4-(4-phenylbutoxy)benzoate. Content: 38.2% Yield: 97% (4-phenyl-1-chlorobutune basis). The organic layer contained methyl 4-methoxybenzoate 0.19% (area percentage). 60 g of he oil layer containing methyl 4-(4-phenylbutoxy)benzoate, 8.5 g of methanol and 18.7 g of 27% by weight aqueous sodium hydroxide solution were mixed, the inside temperature was elevated to 70 to 75° C., and the mixture was stirred at the same temperature for 3 hours to hydrolyze it.

The hydrolyzed liquid was carefully poured into a mixture of 48.7 g of 12.7 wt % sulfuric acid and 42 g of toluene so that the liquid temperature was kept at not more than 70° C., and then the mixture was stirred for 15 minutes. At an inside temperature of 65° C., 5.8 g of 20 wt % sulfuric acid was added thereto to adjust the pH to pH 2.1, and the liquid separation was conducted. 44 g of water was added to the obtained organic layer, and the liquid separation was conducted at an inside temperature of 65° C. and at a pH of 2.1. 44 g of water was added to the obtained organic layer once more, the liquid separation was conducted at an inside temperature of 65° C. and at a pH of 2.1 to give an organic layer containing 4-(4-phenylbutoxy)benzoic acid. Yield: 99.8% (methyl 4-(4-phenylbutoxy)benzoate basis). The organic layer contained 0.17% (area percentage) of 4-methoxybenzoic acid.

INDUSTRIAL APPLICABILITY

The present invention is industrially advantageous, because according to the invention, the carboxylic acid (7) produced as by-products in the reaction can be easily removed to an aqueous layer, and the carboxylic acid compound (3) having a reduced amount of the contaminated carboxylic acid (7) can be obtained.

The invention claimed is:
1. A method for producing a compound represented by the formula (3):

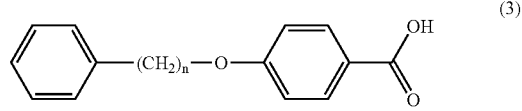

wherein n is an integer of 1 to 6, which method is characterized by the steps of
hydrolyzing a solution containing an ester compound represented by the formula (1):

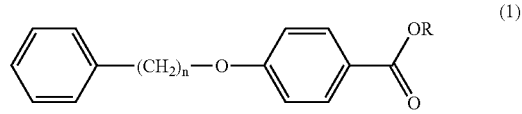

wherein R is a lower alkyl group and n is an integer of 1 to 6, and a compound represented by the formula (2):

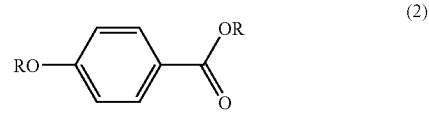

wherein R is as defined above, adjusting the pH of the resulting solution to pH 4 to 8, and then subjecting to phase separation to obtain an organic layer containing the carboxylic acid of formula (3).

2. The method for producing a carboxylic acid compound according to claim 1, wherein the mixture containing the ester compound represented by the formula (1) and the compound represented by the formula (2) is a reaction solution obtained by reacting an ester compound the formula (4)

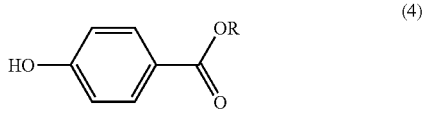

wherein R represents a lower alkyl group, and a halogen compound represented by the formula (5):

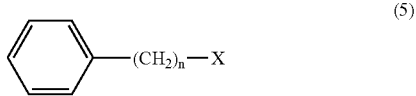

wherein n represents an integer of 1 to 6 and X represents a halogen atom, in an organic solvent in the presence of a base.

3. The method for producing a carboxylic acid compound according to claim 2, wherein the mixture containing the ester compound represented by the formula (1) and the compound represented by the formula (2) is an organic layer obtained by mixing the reaction liquid obtained by reacting the ester compound represented by the formula (4) and the halogen compound represented by the formula (5) in the organic solvent in the presence of a base, water, and optionally a water-insoluble organic solvent; and conducting a liquid phase separation.

4. The method for producing a carboxylic acid compound according to claim 1, wherein n is 4 in the formula (1) of the ester compound.

5. The method for producing a carboxylic acid compound according to claim 2, wherein the reaction is conducted in an aprotonic polar solvent.

6. The method for producing a carboxylic acid compound according to claim 5, wherein the aprotonic polar solvent is N,N-dimethyl formamide, N,N-dimethyl acetamide, N-methyl-2-pyrolidone or dimethyl sulfoxide.

7. The method for producing a carboxylic acid compound according to claim 2, wherein the halogen compound represented by the formula (5) is 4-phenyl-1-chlorobutane.

8. The method for producing a carboxylic acid compound according to claim 1, wherein, the pH of the resulting solution is adjusted to 5 to 7.

* * * * *